US 008765715 B2

(12) United States Patent
Oliver et al.

(10) Patent No.: US 8,765,715 B2
(45) Date of Patent: *Jul. 1, 2014

(54) METHOD OF PROVIDING HEMOSTASIS USING FLEXIBLE BIORESORBABLE FOAM

(71) Applicant: Medtronic Xomed, Inc., Jacksonville, FL (US)

(72) Inventors: Dana A. Oliver, Jacksonville, FL (US); Matthew J. Halversen, Hopkinton, NH (US); Aimee Hodge, Candia, NH (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/682,419

(22) Filed: Nov. 20, 2012

(65) Prior Publication Data

US 2013/0079300 A1 Mar. 28, 2013

Related U.S. Application Data

(62) Division of application No. 11/482,234, filed on Jul. 5, 2006, now Pat. No. 8,313,762.

(51) Int. Cl.
*A61L 24/08* (2006.01)

(52) U.S. Cl.
USPC .......................................................... 514/57

(58) Field of Classification Search
None
See application file for complete search history.

(56) References Cited

U.S. PATENT DOCUMENTS

| 2,914,444 | A | 11/1959 | Smith |
| 3,005,457 | A | 10/1961 | Millman et al. |
| 4,292,972 | A | 10/1981 | Pawelchak et al. |
| 5,017,229 | A | 5/1991 | Burns et al. |
| 5,336,163 | A | 8/1994 | DeMane et al. |
| 5,422,068 | A | 6/1995 | Shalaby et al. |
| 6,923,961 | B2 | 8/2005 | Liu et al. |
| 2003/0187381 | A1 | 10/2003 | Greenwalt et al. |
| 2003/0202970 | A1 | 10/2003 | Liu et al. |
| 2004/0116958 | A1 | 6/2004 | Gopferich et al. |
| 2005/0058632 | A1 | 3/2005 | Hedrick et al. |
| 2005/0123588 | A1 | 6/2005 | Zhu et al. |
| 2005/0260188 | A1 | 11/2005 | Liu et al. |
| 2006/0057182 | A1 | 3/2006 | Oliver et al. |
| 2006/0121086 | A1 | 6/2006 | Boyer et al. |
| 2007/0259029 | A1 | 11/2007 | McEntire et al. |
| 2008/0008738 | A1 | 1/2008 | Oliver et al. |
| 2008/0031929 | A1 | 2/2008 | Baggett |

OTHER PUBLICATIONS

Barbucci et al., "Swellling Behavior of Carboxymethylcellulose Hydrogesl in Relation to Cross-Linking, pH, and Charge Density", Macromolecules, 33:7475-7480 (2000).
Ershov, "Radiation-chemical degradation of cellulose and other polysaccharides", Russian Chemical Reviews, 67 (4):315-334. (1998).
Snitzel et al., "Influcence of Irradiation Sterilization on Polymers Used as Drug Carriers—A Review", Drug Development and Industrial Pharmacy, 23(9):857-878 (1997).
Notice of the Second Office Action (CN 200780026070.2) dated Feb. 4, 2013 (22 pages).

*Primary Examiner* — Robert A Wax
*Assistant Examiner* — William Craigo
(74) *Attorney, Agent, or Firm* — Dicke, Billig & Czaja, PLLC

(57) ABSTRACT

A method of providing hemostasis of bleeding tissue. A flexible bioresorbable foam is formed that consists essentially of carboxymethylcellulose. The flexible bioresorbable foam is crosslinked. Chain scission is performed on the crosslinked flexible bioresorbable foam to provide the flexible bioresorbable foam with a selected in-vivo residence time of between about 3 days and about 14 days. Hemostasis is caused by applying the flexible bioresorbable foam to bleeding tissue. The flexible bioresorbable foam is resorbed in-vivo. The selected in-vivo residence time is a time between the flexible bioresorbable foam being applied to the tissue and the flexible bioresorbable foam having been substantially completely absorbed into the tissue.

26 Claims, No Drawings

METHOD OF PROVIDING HEMOSTASIS USING FLEXIBLE BIORESORBABLE FOAM

CROSS-REFERENCE TO RELATED APPLICATION

This application is a divisional of U.S. patent application Ser. No. 11/482,234, filed Jul. 5, 2006, entitled "Flexible Bioresorbable Hemostatic Packing and Stent"; and the entire teachings of which are incorporated herein by reference.

FIELD OF THE INVENTION

The present invention relates generally to the field of bioresorbable packing and stents, and more specifically to a flexible bioresorbable foam, useful for post-operative or drug delivery use, having both hemostatic properties.

BACKGROUND OF THE INVENTION

Various types of sterile packing and stents are used in the medical and surgical fields for keeping tissues apart or preventing adhesion. Such uses include, but are not limited to, nasal packing and sinus stents, packing for inner ear surgery, tympanoplasty, exostosis, orbital decompression, as well as various orifice restenosis prevention uses. Personal uses such as tampons, bandaging and the like also involved sterile packing materials.

Such packing and stents have been made from gauzes, microfibers, nonfibrous expandable packing, such as tampons, and the like. Resorbable packing and stent devices have also been developed. Such packing materials have typically included hyaluronic acid (HA), or salts of hyaluronic acids, which are naturally occurring mucopolysaccharides found in various body fluids and connective tissues. Thus, HA is biocompatible. It has been adapted for use as a surgical aid to prevent tissue contact and adhesion formation.

Crosslinking has created somewhat insoluble HA materials. Further, other biocompatible materials such as polysaccharides, especially methylcellulosic materials have been combined with the hyaluronic acid to produce packing materials which are resorbable but are also insoluble and have a longer in-vivo residence time before they dissolve into gels and are absorbed by the body tissues. These materials also have increased fluid absorption capabilities.

Collagen is also known for use in the medical field; it is a major protein constituent of connective tissue and is widely used in medical and surgical applications such as sutures, grafts and surgical prostheses. Typical sources include calfskin, bovine Achilles tendons, cattle bones, porcine tissue, human cadaver tissue, and rat tails. Collagen, as an animal protein, is bioresorbable, even when crosslinked to reasonable levels. Collagen is available in a variety of forms including powders and fibrils, and in aqueous solution. Collagen may be provided in insoluble or soluble forms.

It has now been discovered that a flexible bioresorbable foam for packing, post-operative use, and other medical uses may be created having both hemostatic properties and a resorption time of about 14 days (also known as an in-vivo residence time). The foam is formed from carboxymethylcellulose (CMC).

SUMMARY OF THE INVENTION

An embodiment of the invention is directed to a method of providing hemostasis of bleeding tissue. A flexible bioresorbable foam is formed that consists essentially of carboxymethylcellulose. The flexible bioresorbable foam is crosslinked.

Chain scission is performed on the crosslinked flexible bioresorbable foam to provide the flexible bioresorbable foam with a selected in-vivo residence time of between about 3 days and about 14 days. Hemostasis is caused by applying the flexible bioresorbable foam to bleeding tissue.

The flexible bioresorbable foam is resorbed in-vivo. The selected in-vivo residence time is a time between the flexible bioresorbable foam being applied to the tissue and the flexible bioresorbable foam having been substantially completely absorbed into the tissue.

Another embodiment of the invention is directed to a method for preventing adhesion of bleeding tissue. A flexible bioresorbable foam is formed that consists essentially of carboxymethylcellulose. The flexible bioresorbable foam is crosslinked.

Chain scission is performed on the crosslinked flexible bioresorbable foam to provide the flexible bioresorbable foam with a selected in-vivo residence time of between about 3 days and about 14 days. The bleeding tissue is hydrated and separated with the flexible bioresorbable foam to prevent adhesion.

The flexible bioresorbable foam is resorbed in-vivo. The selected in-vivo residence time is a time between the flexible bioresorbable foam being applied to the tissue and the flexible bioresorbable foam having been substantially completely absorbed into the tissue.

Another embodiment of the invention is directed to a method of providing hemostasis of bleeding tissue. A flexible bioresorbable foam is formed that consists essentially of carboxymethylcellulose and a drug. The flexible bioresorbable foam is crosslinked.

Chain scission is performed on the crosslinked flexible bioresorbable foam to provide the flexible bioresorbable foam with a selected in-vivo residence time of between about 3 days and about 14 days. Hemostasis is caused by applying the flexible bioresorbable foam to bleeding tissue.

The flexible bioresorbable foam is resorbed in-vivo. The selected in-vivo residence time is a time between the flexible bioresorbable foam being applied to the tissue and the flexible bioresorbable foam having been substantially completely absorbed into the tissue. The drug is released as the flexible bioresorbable foam is resorbed in-vivo.

These terms when used herein have the following meanings.

The term "bioresorbable" as used herein, means capable of being absorbed by the body.

The term "hemostat" means a device or material which stops blood flow.

The term "stent" means a material or device used for separating tissue and holding it in such separated position.

The term "lyophilizing" means freeze-drying.

The term "resorption time" and "in-vivo residence time" are used interchangeably, and refer to the time between insertion into the body and the time at which the material has been substantially completely absorbed into the tissues.

The term "adhesion" as used herein, refers to the sticking together of tissues which are in intimate contact for extended periods.

The term "dehydrothermal crosslinking" means crosslinking accomplished by application of high temperatures and/or low pressures to a material.

DETAILED DESCRIPTION OF THE INVENTION

The following detailed description describes certain embodiments and is not to be taken in a limiting sense. The scope of the present invention is defined by the appended claims.

The bioresorbable hemostatic packing provided herein may be used in any manner in which sterile packing and/or stents are normally used in the surgical or medical fields, including uses for which control of low volume bleeding and adhesion prevention are important. Such uses include, but are not limited to, nasal packing and sinus stents, packing for inner ear surgery, tympanoplasty, exostosis, orbital decompression, as well as various orifice restenosis prevention uses. The packing materials may also be used as single or combination drug delivery systems for humans or mammals.

Bioresorbable foams of the invention are formed primarily from carboxymethylcellulose. Carboxymethylcellulose is a polyanionic polysaccharide, that is, a polysaccharide containing more than one negatively charged group. Carboxymethylcellulose (CMC) is a derivative of cellulose formed by its reaction with alkali and chloroacetic acid. The CMC structure is based on the $\beta$-(1→4)-D-glucopyranose polymer of cellulose.

Different preparations may have different degrees of substitution, but it is generally in the range 0.6-0.95 derivatives per monomer unit. Carboxymethylcellulose is flexible and soft for ease of handling and contouring within a body cavity, and exhibits the necessary degrees of hydration and expansion to prevent adhesions from forming inside a bodily cavity or in treated bodily tissues. The carboxymethylcellulose expands to at least about 150% of its original dimensions, preferably at least about 200% of its original dimensions.

In one embodiment the bioresorbable foam of the invention is formed from one hundred percent carboxymethylcellulose.

The in-vivo residence times of flexible foams of the invention are typically about 14 days; in many applications, the desirable embodiment of the foam will have an in-vivo residence time of from about 3 days to about 14 days. The in-vivo residence time may be varied as desired by controlling the concentration of the solution used as well as controlling the amount of crosslinking and/or chain scission when forming the carboxymethylcellulose foam.

The foams of the invention are formed by a method which includes formation of a suspension in water. The suspension is formed by mixing with conventional mixers until suspended, being careful to remove large agglomerations. The suspension is mixed, typically at shear rates of from about 0.25 minutes/liter to about 3.0 minutes/liter, and at a speed of from about 7,000 rpm to about 10,000 rpm for processing efficiency. The suspension is then metered into lyophilization trays with a series of cavities. Typical trays have cavities nominally about 6.0 cm by 1.5 cm by 1.0 cm.

The suspended solution is then freeze-dried into solid foam blocks using well known procedures involving vacuum conditions at temperatures which are less than the freezing temperature of water, i.e., less than 0° C. After 0° C. is reached, the temperature is then reduced further over time, and cycled; e.g., the temperature is reduced by a few degrees then maintained at the lower temperature for a period of time, and then reduced again. Finally, the temperature reaches a low of about −45° C. where it is maintained for the period required to complete the lyophilization, e.g., at least about 10 hours, and perhaps as much as 24-30 hours.

The drying portion of the lyophilization is performed at a vacuum set point in a range from about 10 to about 500 mm of mercury. In one process, the vacuum set point is about 75 mm of mercury (Hg), with the temperature being raised in a controlled fashion. In one process, the temperature is maintained at 0° C. for at least about 2 hours, and up to about 6 hours, then raised to at least about 25° C. to a period of from about 4 hours to about 40 hours.

Upon completion of lyophilization, the foam is then ready to be crosslinked. Crosslinking may be accomplished by dehydrothermal crosslinking, or by exposure to a chemical crosslinking agent. In dehydrothermal crosslinking, the foam is dehydrated to reduce the moisture content to the temperature at which crosslinking occurs, typically to less than about 1% by weight. The product is subjected to elevated temperatures and/or vacuum conditions until crosslinking occurs.

Useful combinations of such conditions include vacuum of at least about $10^{-5}$ mm of mercury, and temperatures of at least about 35° C. Naturally, if vacuum is not used, much higher temperatures are required, e.g., above 75° C. The conditions are maintained for at least about 10 hours, typically for about 24 hours until the desired molecular weight has been achieved.

Effective crosslinking can be accomplished by exposure to temperatures of about 115° C. to about 125° C. for periods of about three (3) to about four (4) hours. Sterilization typically occurs after exposure of about three (3) to about four (4) hours at 160° C. or for periods of from about 24 hours to about forty (40) hours at a temperature of about 125° C.

If chemical crosslinking is desired, useful chemical crosslinking agents include aldehydes, e.g., formaldehyde vapor, which can be used by pumping it into a container or a room containing the lyophilized foam and allowed to contact the foam for at least about 2 hours, preferably at least about 5 hours. After the desired exposure time is complete, the crosslinking agent is evacuated from the container or room.

The bioresorbable foam of the invention can be easily handled either wet or dry and may be squeezed, and/or cut to required size. The foam will contour to the body cavity or wound as required, and provides mechanical/chemical hemostasis as well as preventing adhesion, and minimizing swelling and edema.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, biomedical, and biomaterials arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

The invention claimed is:

1. A method of providing hemostasis of bleeding tissue, wherein the method comprises:
   forming a flexible bioresorbable foam that consists essentially of carboxymethylcellulose;
   crosslinking the flexible bioresorbable foam;
   performing chain scission on the crosslinked flexible bioresorbable foam to provide the flexible bioresorbable foam with a selected in-vivo residence time of between about 3 days and about 14 days;
   causing hemostasis by applying the flexible bioresorbable foam to bleeding tissue; and
   resorbing the flexible bioresorbable foam in-vivo, wherein the selected in-vivo residence time is a time between the flexible bioresorbable foam being applied to the tissue and the flexible bioresorbable foam having been substantially completely absorbed into the tissue.

2. The method of claim 1, and further comprising inserting the flexible bioresorbable foam into a cavity or orifice of a living body to separate opposing tissue surfaces and prevent adhesion.

3. The method of claim 2, wherein the cavity is a nasal/sinus cavity, otologic cavity, a cranial cavity, a thoracic cavity, an abdominal cavity, a pelvic cavity, an eye cavity, an ear cavity, a nose cavity or a throat cavity.

4. The method of claim 1, wherein forming dries the flexible bioresorbable foam to a moisture content of less than about 1% by weight.

5. The method of claim 1, wherein forming the flexible bioresorbable foam comprises:
mixing carboxymethylcellulose with water to form a suspension; and
freezing and lyophilizing the suspension at a temperature of less than about 0° C.

6. The method of claim 1, and further comprising sterilizing the flexible bioresorbable foam.

7. The method of claim 6, wherein the crosslinking and sterilizing are done at a temperature of between about 115° C. and about 125° C. for between about 3 hours and about 4 hours.

8. The method of claim 6, wherein the sterilizing and the performing chain scission are done by bombardment with gamma rays or electron beams.

9. The method of claim 1, wherein during the forming process, the flexible bioresorbable foam expands to at least about 150% of an initial volume of the carboxymethylcellulose.

10. The method of claim 1, wherein the flexible bioresorbable foam consists of 100% carboxymethylcellulose.

11. A method for preventing adhesion of bleeding tissue, wherein the method comprises:
forming a flexible bioresorbable foam that consists essentially of carboxymethylcellulose;
crosslinking the flexible bioresorbable foam;
performing chain scission on the crosslinked flexible bioresorbable foam to provide the flexible bioresorbable foam with a selected in-vivo residence time of between about 3 days and about 14 days;
hydrating and separating the bleeding tissue with the flexible bioresorbable foam to prevent adhesion; and
resorbing the flexible bioresorbable foam in-vivo, wherein the selected in-vivo residence time is a time between the flexible bioresorbable foam being applied to the tissue and the flexible bioresorbable foam having been substantially completely absorbed into the tissue.

12. The method of claim 11, and further comprising inserting the flexible bioresorbable foam into a cavity or orifice of a living body to separate opposing tissue surfaces and prevent adhesion.

13. The method of claim 12, wherein the cavity is a nasal/sinus cavity, otologic cavity, a cranial cavity, a thoracic cavity, an abdominal cavity, a pelvic cavity, an eye cavity, an ear cavity, a nose cavity or a throat cavity.

14. The method of claim 11, wherein forming the flexible bioresorbable foam comprises:
mixing carboxymethylcellulose with water to form a suspension; and
freezing and lyophilizing the suspension at a temperature of less than about 0° C.

15. The method of claim 11, and further comprising sterilizing the flexible bioresorbable foam.

16. The method of claim 15, wherein the crosslinking and sterilizing are done at a temperature of between about 115° C. and about 125° C. for between about 3 hours and about 4 hours.

17. The method of claim 15, wherein the sterilizing and the performing chain scission are done by bombardment with gamma rays or electron beams.

18. The method of claim 15, wherein the flexible bioresorbable foam consists of 100% carboxymethylcellulose.

19. A method of providing hemostasis of bleeding tissue, wherein the method comprises:
forming a flexible bioresorbable foam that consists essentially of carboxymethylcellulose and a drug;
crosslinking the flexible bioresorbable foam;
performing chain scission on the crosslinked flexible bioresorbable foam to provide the flexible bioresorbable foam with a selected in-vivo residence time of between about 3 days and about 14 days;
causing hemostasis by applying the flexible bioresorbable foam to bleeding tissue;
resorbing the flexible bioresorbable foam in-vivo, wherein the selected in-vivo residence time is a time between the flexible bioresorbable foam being applied to the tissue and the flexible bioresorbable foam having been substantially completely absorbed into the tissue; and
releasing the drug as the flexible bioresorbable foam is resorbed in-vivo.

20. The method of claim 19, and further comprising inserting the flexible bioresorbable foam into a cavity or orifice of a living body to separate opposing tissue surfaces and prevent adhesion.

21. The method of claim 20, wherein the cavity is a nasal/sinus cavity, otologic cavity, a cranial cavity, a thoracic cavity, an abdominal cavity, a pelvic cavity, an eye cavity, an ear cavity, a nose cavity or a throat cavity.

22. The method of claim 19, wherein forming the flexible bioresorbable foam comprises:
mixing carboxymethylcellulose with water to form a suspension; and
freezing and lyophilizing the suspension at a temperature of less than about 0° C.

23. The method of claim 19, and further comprising sterilizing the flexible bioresorbable foam.

24. The method of claim 23, wherein the crosslinking and sterilizing are done at a temperature of between about 115° C. and about 125° C. for between about 3 hours and about 4 hours.

25. The method of claim 23, wherein the sterilizing and the performing chain scission are done by bombardment with gamma rays or electron beams.

26. The method of claim 19, wherein the flexible bioresorbable foam consists of 100% carboxymethylcellulose.

* * * * *